US008883830B2

(12) United States Patent
Aung-Din

(10) Patent No.: US 8,883,830 B2
(45) Date of Patent: *Nov. 11, 2014

(54) TOPICAL THERAPY FOR THE TREATMENT OF MIGRAINES, MUSCLE SPRAINS, MUSCLE SPASMS, SPASTICITY AND RELATED CONDITIONS

(75) Inventor: Ronald Aung-Din, Sarasota, FL (US)

(73) Assignee: Afgin Pharma LLC., Sarasota, FL (US)

( * ) Notice: Subject to any disclaimer, the term of this patent is extended or adjusted under 35 U.S.C. 154(b) by 93 days.

This patent is subject to a terminal disclaimer.

(21) Appl. No.: 13/349,849

(22) Filed: Jan. 13, 2012

(65) Prior Publication Data

US 2012/0114741 A1 May 10, 2012

Related U.S. Application Data

(63) Continuation of application No. 10/560,889, filed as application No. PCT/US2004/019816 on Jun. 21, 2004, now abandoned.

(60) Provisional application No. 60/480,089, filed on Jun. 20, 2003, provisional application No. 60/480,088, filed on Jun. 20, 2003, provisional application No. 60/513,082, filed on Oct. 21, 2003.

(51) Int. Cl.

| A01N 43/82 | (2006.01) |
|---|---|
| A61K 31/41 | (2006.01) |
| A01N 43/38 | (2006.01) |
| A61K 31/405 | (2006.01) |
| A61K 31/44 | (2006.01) |
| A01N 43/42 | (2006.01) |
| A01N 43/58 | (2006.01) |
| A01N 43/60 | (2006.01) |
| A61K 31/50 | (2006.01) |
| A61K 31/495 | (2006.01) |
| A61K 47/10 | (2006.01) |
| A61K 47/14 | (2006.01) |
| A61K 9/00 | (2006.01) |
| A61K 31/445 | (2006.01) |
| A61K 31/455 | (2006.01) |
| A61K 31/48 | (2006.01) |
| A61K 31/55 | (2006.01) |
| A61K 45/06 | (2006.01) |
| A61K 31/551 | (2006.01) |
| A61K 47/24 | (2006.01) |
| A61K 9/06 | (2006.01) |
| A61K 47/44 | (2006.01) |
| A61K 31/498 | (2006.01) |

(52) U.S. Cl.
CPC ............... *A61K 31/55* (2013.01); *A61K 47/10* (2013.01); *A61K 47/14* (2013.01); *A61K 9/0014* (2013.01); *A61K 31/445* (2013.01); *A61K 31/455* (2013.01); *A61K 31/48* (2013.01); *A61K 45/06* (2013.01); *A61K 31/551* (2013.01); *A61K 47/24* (2013.01); *A61K 9/06* (2013.01); *A61K 47/44* (2013.01); *A61K 31/498* (2013.01)

USPC ............ 514/362; 514/415; 514/288; 514/250

(58) Field of Classification Search
CPC .................................................... A61K 31/433
USPC ................... 514/362, 415, 288, 250
See application file for complete search history.

(56) References Cited

U.S. PATENT DOCUMENTS

| 3,598,122 A | 8/1971 | Zaffaroni |
|---|---|---|
| 3,797,494 A | 3/1974 | Zaffaroni |
| 3,854,480 A | 12/1974 | Zaffaroni |
| 4,144,317 A | 3/1979 | Higuchi et al. |
| 4,201,211 A | 5/1980 | Chandrasekaran et al. |
| 4,244,949 A | 1/1981 | Gupta |
| 4,262,003 A | 4/1981 | Urquhart et al. |
| 4,379,454 A | 4/1983 | Campbell et al. |
| 4,491,664 A | 1/1985 | Oppolzer |
| 4,511,563 A | 4/1985 | Schmolka |
| 4,588,580 A | 5/1986 | Gale et al. |
| 4,767,619 A | 8/1988 | Murray |
| 4,806,341 A | 2/1989 | Chien et al. |
| 4,816,470 A | 3/1989 | Dowie et al. |
| 4,820,720 A | 4/1989 | Sanders et al. |
| 4,861,760 A | 8/1989 | Mazuel et al. |
| 4,883,660 A | 11/1989 | Blackman et al. |
| 4,916,132 A | 4/1990 | Seibel |
| 5,016,652 A | 5/1991 | Rose et al. |

(Continued)

FOREIGN PATENT DOCUMENTS

| EP | 0303507 | 2/1989 |
|---|---|---|
| EP | 0500086 | 8/1992 |

(Continued)

OTHER PUBLICATIONS

Saper et al. 2002, Headache, vol. 42, pp. 470-482.*
Aung-Din et al. 2001, Cephalalgia, vol. 21, pp. 405-432.*
U.S. Appl. No. 12/460,966, filed Jul. 2009, Aung-Din.*
U.S. Appl. No. 13/707,863, filed Dec. 2012, Aung-Din.*
Messlinger, K;Hotta,H.; Pawlak, M.;Schmidt, R.F., Effects of the 5-HT1 receptor agonists, sumatriptan and CP 93,129, on dural arterial flow in the rat, Eur J Pharmacol, vol. 332 No. 2, Aug 6, 1997 pp. 173-181.
Piovesan, et al., "Referred Pain After Painful Stimulation of the Greater Occipital Nerve in Humans: Evidence of Convergence of Cervical Afferences on Trigeminal Nuclei", Cephalalgia, 2001, 21, 107-109.
Rougier, et al. In vivo percutaneous penetration of some organic compounds related to anatomic site in humans; predictive assessment by the stripping method, J. Pharmac. Sci., vol. 76, No. 6, Jun. 1987, pp. 451-454.

(Continued)

*Primary Examiner* — Kara R McMillian
(74) *Attorney, Agent, or Firm* — Davidson, Davidson & Kappel, LLC

(57) ABSTRACT

The invention is directed to topical formulations and methods of treating a migraines and/or cluster headaches, muscle sprains, muscle spasms, spasticity, tension headaches, tension related migraines and related conditions associated with muscle tension and pain with a therapeutically effective amount of an ergot alkaloid, skeletal muscle relaxant, serotonin agonist, combinations thereof, pharmaceutically acceptable salt thereof, prodrugs thereof or derivative thereof.

20 Claims, No Drawings

(56) References Cited

U.S. PATENT DOCUMENTS

| | | | |
|---|---|---|---|
| 5,026,556 A | 6/1991 | Drust et al. | |
| 5,037,845 A * | 8/1991 | Oxford | 514/415 |
| 5,053,227 A | 10/1991 | Chiang et al. | |
| 5,059,426 A | 10/1991 | Chiang et al. | |
| 5,069,909 A | 12/1991 | Sharma et al. | |
| 5,307,953 A | 5/1994 | Regan | |
| 5,318,780 A | 6/1994 | Viegas et al. | |
| 5,364,628 A | 11/1994 | Kissel et al. | |
| 5,466,699 A | 11/1995 | Robertson et al. | |
| 5,521,196 A | 5/1996 | Audia et al. | |
| 5,545,644 A | 8/1996 | Macor et al. | |
| 5,554,639 A | 9/1996 | Craig et al. | |
| 5,562,917 A | 10/1996 | Durif et al. | |
| 5,601,835 A | 2/1997 | Sabel et al. | |
| 5,698,571 A | 12/1997 | Audia et al. | |
| 5,705,520 A | 1/1998 | Craig et al. | |
| 5,719,197 A | 2/1998 | Kanios et al. | |
| 5,744,482 A | 4/1998 | Cohen et al. | |
| 5,807,571 A | 9/1998 | List | |
| 5,814,653 A | 9/1998 | Flaugh et al. | |
| 5,837,289 A | 11/1998 | Grasela et al. | |
| 5,855,907 A | 1/1999 | Peyman | |
| 5,863,559 A | 1/1999 | Phillips et al. | |
| 5,863,935 A | 1/1999 | Robertson et al. | |
| 5,872,145 A | 2/1999 | Plachetka | |
| 5,891,885 A | 4/1999 | Caruso | |
| 5,897,880 A * | 4/1999 | Drizen et al. | 424/488 |
| 5,939,425 A | 8/1999 | Caruso | |
| 5,968,542 A | 10/1999 | Tipton | |
| 6,020,001 A | 2/2000 | Phillips et al. | |
| 6,043,244 A | 3/2000 | Caruso | |
| 6,060,499 A | 5/2000 | Plachetka | |
| 6,103,266 A | 8/2000 | Tapolsky et al. | |
| 6,194,432 B1 | 2/2001 | Sheftell et al. | |
| 6,197,331 B1 | 3/2001 | Lerner et al. | |
| 6,287,588 B1 | 9/2001 | Shih et al. | |
| 6,368,627 B1 | 4/2002 | Phillips et al. | |
| 6,383,471 B1 | 5/2002 | Chen et al. | |
| 6,384,034 B2 | 5/2002 | Simitchieva et al. | |
| 6,455,557 B1 | 9/2002 | Pellegrini et al. | |
| 6,495,535 B1 * | 12/2002 | Plachetka et al. | 514/177 |
| 6,576,263 B2 | 6/2003 | Truong et al. | |
| 6,689,379 B1 | 2/2004 | Bracht | |
| 6,962,691 B1 | 11/2005 | Lulla et al. | |
| 7,314,636 B2 | 1/2008 | Caseres et al. | |
| 7,332,503 B2 | 2/2008 | Wikstrom et al. | |
| 7,354,420 B2 | 4/2008 | Steil et al. | |
| 7,364,568 B2 | 4/2008 | Angel et al. | |
| 7,754,240 B2 | 7/2010 | Staniforth et al. | |
| 2002/0015713 A1* | 2/2002 | Murdock et al. | 424/400 |
| 2002/0132827 A1 | 9/2002 | Nichols et al. | |
| 2003/0013753 A1 | 1/2003 | Aung-Din | |
| 2003/0167556 A1 | 9/2003 | Kelley et al. | |
| 2003/0232805 A1* | 12/2003 | Kranzler et al. | 514/217 |
| 2004/0219172 A1* | 11/2004 | Voet | 424/239.1 |
| 2004/0220205 A1 | 11/2004 | Wikstrom | |
| 2007/0065463 A1 | 3/2007 | Aung-Din | |
| 2007/0203209 A1 | 8/2007 | Bartolini et al. | |
| 2007/0275964 A1 | 11/2007 | Griffith et al. | |
| 2008/0038363 A1 | 2/2008 | Zaffaroni et al. | |
| 2011/0021596 A1 | 1/2011 | Aung-Din | |
| 2011/0178114 A1 | 7/2011 | Aung-Din | |

FOREIGN PATENT DOCUMENTS

| | | |
|---|---|---|
| EP | 0636623 | 2/1995 |
| EP | 0705600 | 10/1996 |
| EP | 02739657 | 4/2005 |
| GB | 2098865 A * | 12/1982 |
| WO | WO 9011756 | 10/1990 |
| WO | 9118897 | 12/1991 |
| WO | 9206973 | 4/1992 |
| WO | 9426270 | 11/1994 |
| WO | 9505137 | 2/1995 |
| WO | 03024456 | 3/2003 |
| WO | 03032983 | 4/2003 |
| WO | 2004112723 | 12/2004 |
| WO | WO 2007128462 A1 | 11/2007 |
| WO | WO 2010/005507 | 1/2010 |

OTHER PUBLICATIONS

Goodman & Gilman, The Pharmacological Basis of Therapeutics, Ninth Edition,(1996), Chapter 21, Peroutka, Drugs Effective in the Therapy of Migraine, pp. 487-502.
Methods Find Exp Clin Pharmaco12002, 24(6): 371-391 •Gateways to Clinical Trials•Jul.-Aug. 2002 M. Bayes, X. Rabasseda, J.R.Prous.
Schwarz, et al., Postdural Puncture Headache: Diagnosis, Prevention and Therapy Schmerz, vol. 13, No. 5, 1999—pp. 332-340.
Aung-Din, Ronald, Transdermal Sumatriptan: A Novel Dosage Form Efficacious in the Treatment of Acute Migraine, Headache: The Journal of Head and Face Pain,vol. 45,No. 5, pp. 389-390; May 2002.
Aung-Din, Ronald, Transdermal Sumatriptan in Clinical Practice: The Experience of 42 Patients with Acute Migraine in an Outpatient Setting, Headache: The Journal of Head and Face Pain, vol. 43,No. 5, p. 523; May 2003.
Aung-Din, Ronald and Kinnard, Fred, Topical Tizanidine (Zanaflex) Gel Effective in Migraine and Tension-Type Headache, Headache: The Journal of Head and Face Pain, vol. 44, No. 5, p. 509; May 2004.
Norton,Patrice G.W., Transdermal Sumatriptan May Relieve Migraines, Internal Medicine News, vol. 36, Issue 19, p. 14, Oct. 1, 2003.
Bartsch,T. and Goadsby P.J.,"Increased responses in trigeminocervicalnociceptive neurons to cervicalinput after stimulation of the dura mater", Brain, vol. 126,No. 8, 1801-1813, Aug. 2003.
Bogduk,Nikolai,MD,PhD, "Cervicogenic Headache: Anatomic Basis and Pathophysiologic Mechanisms", Current Pain and Headache Reports, 5: 382-386, 2001.
Aung-Din, Ronald, MD, "Topical Delivery: Topical Regional Neuro-Affective ITRNAI Therapy: Novel Ground-Breaking Triptan Drug Delivery for Treating Migranes",Drug Delivery Technology,Sep. 2009, vol. 9, No. 8.
Pierce, Market al, "Zelrix: a novel transdermal formulation of sumatriptan" Headache, vol. 49, Jun. 2009, pp. 817-825; Abstract.
Patel,SR et al, "Controlled non-invasive transdermal iontophoretic delivery of zolmitriptan hydrochloride in vitro and in vivo" Eur. J. Pharm. And Biopharm, vol. 72, Feb. 2009, pp. 304-309; Abstract.
Garg, T et al, "Elastic liposomal formulation for sustained delivery of antimigraine drug: in vitro characterization and biological evaluation" Drug Dev.Ind. Pharm . . . , vol. 34, Oct. 2008, pp. 1100-1110.
Tennant, F., "Topical Use of Morphine", Practical Pain Management, Oct. 2008, pp. 42-43.
Remington's Pharmaceutical Sciences, 15 111 edition, 1975, Mack Publishing Co. p. 1529.
Chepyala et al., Treatment of Cyclic Vomiting Syndrome, Current Treatment Options in Gastroenterology, 2007, 10: abstract only.
Katzenschlager et. al., Movement Disorders, 2005, Movement Disorder Society, vol. 20, No. 2, pp. 151-157.
Merello et. al., Journal of Neurology, Neurosurgery, and Psychiatry, 1994, BMJ Publishing Group, vol. 57, pp. 1503-1509.
Trojanowski et. al., Annals of the New York Academy of Sciences, 2003, New York Academy of Sciences, vol. 991, pp. 107-110.
CAS STN abstract; Reches et. al., Advances in Neurology, 1984, vol. 40, pp. 171-179.
Cousins et. al., European Journal of Pharmacology, 1997, Elsevier, vol. 322, pp. 137-145.
Aung-Din, R. et al, "Transdermal sumatriptan: effectiveness and convenience in migraineurs," Blackwell Science Ltd. Cephalalgia, 2001, 21, 412.
Diagnose, Prophylaxe and Therapie - Postpunktioneller Kopfschmerz—Schmerz 1999—13-332-340 © Springer-Verlag 199, Abstract Only.
Siegel and Langer, "Controlled release of polypeptides and other macromolecules", Pharmaceutical Research 1, 2-10 (1984).

\* cited by examiner

TOPICAL THERAPY FOR THE TREATMENT OF MIGRAINES, MUSCLE SPRAINS, MUSCLE SPASMS, SPASTICITY AND RELATED CONDITIONS

BACKGROUND OF THE INVENTION

The present invention is directed to methods and formulations for treating migraines, muscle sprains, muscle spasms, spasticity, tension headache, tension-related migraines and related conditions associated with muscle tension and pain.

Migraine headaches are a debilitating condition in which some 53 million persons per year suffer acute pain. Frequently, migraine is accompanied by sickness and vomiting and a sensitivity to light and noise.

Several theories on the pathogenesis of migraine have been hypothesized and include: i) the vascular theory (i.e., migraine is a vasospastic disorder that is initiated by vasoconstriction in the cranial vasculature); ii) the cortical spreading depression theory (i.e., CSD begins with a brief wave of excitation, followed by a prolonged period of neuronal depression, which is associated with disturbances in nerve cell metabolism and regional reductions in blood flow); iii) the neurovascular hypothesis (i.e., migraine triggers or CSD can activate trigeminal nerve axons, which then release neuropeptides, such as substance P, neurokinin A, and CGRP) from axon terminals near the meningeal and other blood vessels that produce an inflammatory response in the area around the innervated blood vessels); iv) the serotonergic abnormalities hypothesis (i.e., proposes that serotonin may be involved in the pathogenesis of migraine due to observations that both plasma and platelet levels of serotonin fluctuate during a migraine attack, an initial surge in plasma serotonin levels may cause constriction of cerebral blood vessels and a reduction in cerebral blood flow. If the blood flow is sufficiently reduced, migraine aura may result); and v) the integrated hypothesis (i.e., triggers such as stress, glare, noise, the patient's internal clock, the dilation of the internal or external carotid arteries, or other factors may activate specific centers in the brain stem causing migraine).

Muscle sprains, muscle spasms, spasticity, tension headaches and tension-related migraines are also common debilitating conditions that are associated with acute pain, chronic pain and involuntary movement that can be so severe that the condition(s) frequently disrupt an individual's daily life.

Muscle spasm may occur as a result of direct soft tissue trauma with spasm of injured muscles. It may also arise as a consequence of spinal nerve root irritation from musculoskeletal injury. Para spinal muscles are primarily affected in this situation, so called "cervical and lumbar sprains." Muscle spasm can manifest as a sudden involuntary contraction of one or more muscle groups and is usually an acute condition associated with muscle strain (partial tear of a muscle) or sprain (partial or complete rupture of a ligament). Spasticity is a state of increased muscular tone with exaggeration of the tendon reflexes from an upper motor neuron (brain or spinal cord) injury in which spinal inhibitory processes are suppressed or lost. The result is chronic, severe spasm of the muscles of the extremities hindering function and causing pain. Spasticity is often associated with illnesses such as multiple sclerosis, stroke and spinal cord injury. Tension headaches and tension-related migraines are a result of over activity of muscles of the scalp, forehead and neck.

Ergot is the product of a fungus that grows most predominantly on rye with other grains being affected. Since the discovery of ergot and ergot alkaloids over four hundred years ago, the cumulative results of many diverse studies have indicated that ergot alkaloids play a significant role in the functioning of the mammalian body. For example, the pharmacological effects of ergot alkaloids on the uterus, cardiovascular system, smooth muscles and vasculature have been studied.

Ergot alkaloids pharmacological actions are complex due to their effects on several different receptors. However, clinical applications for ergot alkaloids have been studied in various disease states and medical conditions, e.g., Parkinson's disease and post-partum hemorrhage. One particular area where the therapeutic use of ergot alkaloids has received particular attention is in the treatment of migraines.

Ergot alkaloids have been used for treating migraines since the 1920s and their continued use for the acute relief of moderate or severe migraine is still being studied today. The ergot alkaloids possess varied and complex pharmacological actions due to there ability to act as partial agonists or antagonists at $5HT_1$ and $5HT_2$ receptors as well as adrenergic, dopaminergic and tryptaminergic receptors. The spectrum of their effects depends upon the agent(s), dosage, species, tissue, and experimental or physiological conditions. It is because of the ergot alkaloids multiple pharmacological effects on the various receptors that their exact mechanism of action for treating migraine is uncertain.

In the prior art, ergot alkaloids have been used for the local treatment of various disease states and conditions.

For example, U.S. Pat. No. 4,916,132 to Seibel describes dihydroergotamine compositions and methods of preparing the same for use in the local treatment of trophic disturbances, e.g., stasis dermatoses, ulcers and tissue death.

Additionally, U.S. Published Patent Application No. 2002/0042438 to Pelletier et al. describes a method of reducing or inhibiting the glycation of skin proteins, in particular, for preventing or treating the signs of ageing of the skin and/or the orange-peel appearance of the skin and for slimming and/or refining the silhouette and contours of the face, by topically applying a composition containing an ergothioneine or derivative thereof to the skin of a person.

As with the ergot alkaloids, many diverse studies utilizing serotonin (5 hydroxytryptamine, 5-HT) have indicated that serotonin plays a significant role in the functioning of the mammalian body, both in the central nervous system and in peripheral systems as well. Morphological studies of the central nervous system have shown that serotonergic neurons, which originate in the brain stem, form a very diffuse system that projects to most areas of the brain and spinal cord. R. A. O'Brien, Serotonin in Mental Abnormalities, 1: 41 (1978); H. W. M. Steinbusch, HANDBOOK OF CHEMICAL NEUROANATOMY, Volume 3, Part II, 68 (1984); N. E. Anden, et al., Acta Physiological Scandinavia, 67: 313 (1966). These studies have been complemented by biochemical evidence that indicates large concentrations of 5-HT exist in the brain and spinal cord. H. W. M. Steinbusch, supra.

Serotonin (5-hydroxytryptamine, 5-HT) is said to play a key role in regulating the vascular tone, and serotonin deficiency is said to result in a vasodilatation causing the migrainous headache. The onset of action is affected via $5-HT_1$- receptors in the region of the vascular walls of cerebral arteries.

Accordingly, in the last few years, the chemical structure of serotonin has been modified in various manners, resulting in changes of the pharmacological properties. For example, indole derivatives were synthesized which cause the cerebral vessels to be selectively tonizised (contracted) combined with a rapid improvement of the symptoms. These are so-called serotonin agonists having a particular affinity for $5-HT_1$- receptors.

The class of serotonin agonists having a particular affinity for 5-HT$_1$ receptors are typified, for example, by sumatriptan, zolmitriptan, naratriptan, and rizatriptan to name a few. Oral bioavailability is an important factor in the efficacy of a drug and one that may account for consistency of response with repeated use. Sumatriptan tablets have a low oral bioavailability (14%). All of the second-generation triptans have improved bioavailability (rizatriptan and zolmitriptan, 40-45%; naratriptan, close to 70%). Sumatriptan, rizatriptan, and zolmitriptan are metabolized by the MAO system. All of these compounds, however, have some adverse effects which require supervised administration at efficacious doses. PHYSICIAN'S DESK REFERENCE, (48th ed., 1994).

In the prior art, there have been previous attempts to provide for a more efficacious and safe treatment using serotonin agonists specific for the treatment of 5-HT$_1$ receptor subtype.

For Example, U.S. Pat. No. 5,863,935 to Robertson et al. describes certain compounds having "5-HT$_1$-like" receptor agonist properties and their administration in a number of ways, including topical or intranasal application.

Additionally, U.S. Pat. No. 5,805,571 to List, describes a transdermal therapeutic system for the systemic administration of active substances wherein at least one of the active substances listed is a serotonin agonist of the group comprising indole derivatives. Typically, transdermal systems are not used in acute situations because they do not provide an immediate effect, but rather provide prophylaxis or prolonged effect. Transdermal systems such as that described in the '571 patent to List require a period of time for the drug to pass through a barrier layer and onto/into the skin which may take e.g., a substantial period of time until the dose of drug that is absorbed is sufficient to alleviate the pain associated with the headache.

Skeletal muscle relaxants have played a significant role in alleviating stiffness, pain, and discomfort caused by muscle sprains, muscle spasms, spasticity, tension headache and tension-related migraines. Their mechanism of action can be attributed to their direct effect on skeletal muscles (e.g., direct acting skeletal muscle relaxants such as dantrolene) or their ability to reduce spasticity by increasing pre-synaptic inhibition of motor neurons, inhibiting monosynaptic or polysynaptic reflexes at the spinal level (e.g., centrally acting skeletal muscle relaxants such as tizanindine and baclofen).

Most skeletal muscle relaxants are centrally acting and are administered via the oral route or parenteral route. The drawback of the oral or parenteral administration is that there are frequent systemic side effects such as fatigue, lethargy, weakness and mental clouding, particularly as higher doses are reached. Benzodiazepines, e.g., diazepam, have additional drawbacks such as tolerance, psychological dependency and withdrawal effects, e.g., seizures. Oral administration route also entails delay of drug effect through gastrointestinal absorption and systemic circulation.

In certain instances skeletal muscle relaxants can also be administered topically. For example, U.S. Pat. No. 5,364,628 to Kissel et al. describes a transdermal adhesive plaster or patch containing tizanidine for application every three days for the systemic treatment of rheumatic pains and muscle spasms. Also, UK Patent Application No. 2098865 to Joachim Franz et al. describes a composition and method for administering a sustained release micro emulsion containing tizanidine. A suitable dose of 10-50 mg of tizanidine may be administered, which provides an effect for up to three (3) days. Although topical administration has been described in the art, FDA approval has only been granted for oral and parenteral administration of skeletal muscle relaxants.

SUMMARY OF THE INVENTION

It is an object of the present invention to provide a topical formulation and method for the treatment of migraines and/or cluster headaches in humans via the topical administration of a therapeutically effective amount of an active agent(s).

It is an object of the present invention to provide a topical formulation and method for the treatment of muscle sprains, muscle spasms, spasticity, tension headaches, tension-related migraines and related conditions associated with muscle tension and pain in humans via the topical administration of an active agent(s).

It is an object of certain embodiments of the present invention to provide a topical therapeutic formulation and method for the systemic and/or regional administration of a therapeutically effective amount of an active agent(s).

It is an object of certain embodiments of the present invention to provide a more rapid therapeutic effect than previous routes of administration of a therapeutically effective amount of an active agent(s) for the treatment of migraines and/or cluster headaches, muscle sprains, muscle spasms, spasticity, tension headaches, tension-related migraines and related conditions associated with muscle tension and pain.

It is another object of certain embodiments of the present invention to provide a topical formulation for the treatment of migraines and/or cluster headaches, muscle sprains, muscle spasms, spasticity, tension headaches, tension-related migraines and related conditions associated with muscle tension and pain in humans with an active agent(s) that provides a more rapid therapeutic effect than previous routes of administration of the active agent(s). In certain other embodiments, the active agent(s) provide a localized effect and/or reduced side effects.

The above objects and others are attained by virtue of the present invention, which is directed in part to a topical formulation for the treatment of migraines and/or cluster headaches, muscle spasms, muscle sprains, spasticity, tension headaches, tension-related migraines and related conditions associated with muscle tension and pain comprising a dose of an active agent(s) in an effective concentration to provide a therapeutic localized effect when the dose of the active agent(s) is applied to the skin of a human patient, and at least one pharmaceutically acceptable excipient for topical application. In certain preferred embodiments, the active agent is selected from the group consisting of an ergot alkaloid, a serotonin agonist and a skeletal muscle relaxant.

In certain embodiments, the present invention is directed to a method of treating migraines and/or cluster headaches comprising topically applying an active agent(s) to the headache region of a human patient in an effective amount to provide relief of a migraine and/or cluster headache which is occurring or imminent in the human patient.

In certain embodiments, the present invention is further directed to a method of treating migraines, cluster headaches, muscle sprains, muscle spasms, spasticity, tension headaches and tension related migraines with a topical formulation comprising applying a unit dose of a therapeutically effective amount of an active agent(s) incorporated into a pharmaceutically acceptable excipient onto the skin of a human patient, the unit dose comprising an active agent(s) being selected from the group consisting of: i) an ergot alkaloid; ii) a skeletal muscle relaxant; or iii) a combination of an ergot alkaloid and a skeletal muscle relaxant, the unit dose providing a therapeutic effect within about 2 hours after topical administration to the human patient.

In certain embodiments, the present invention is further directed to a method for treating a migraines and/or cluster headache comprising applying a unit dose of an active agent(s) effective for treating a migraine or cluster headache incorporated into a pharmaceutically acceptable excipient for topical administration onto the skin of a human patient; the unit dose providing the active agent(s) in an effective concentration in the excipient such that the unit dose when applied to a headache region of a human patient provides relief from a migraine or cluster headache within about 2 hours after topical administration to the human patient.

In certain embodiments, the present invention is further directed to a method for treating muscle sprains, muscle spasms, spasticity, tension headaches, tension-related migraines and related conditions associated with muscle tension and pain comprising applying a unit dose of a topical formulation for the acute treatment of muscle sprains, muscle spasms, spasticity, tension headaches, tension-related migraines and related conditions associated with muscle tension and pain; the unit dose comprising an active agent(s) incorporated into a pharmaceutically acceptable excipient; the topical preparation providing for the immediate delivery of an effective amount of the active agent(s) for absorption when the unit dose is applied to a region of a human patient experiencing muscle sprains, muscle spasms, spasticity, tension headache and/or tension-related migraines.

In certain embodiments, the methods of the present invention further include applying an additional dose of an active agent(s) to the region experiencing migraine and/or cluster headache, muscle sprain, muscle spasm, spasticity, tension headache and/or tension-related migraines about 15 minutes to about 3 hours after the first application of the active agent(s), preferably 30 minutes to about 2 hours after the first application of the active agent(s), and most preferably from about 30 minutes to about 1 hour after the first application of the active agent(s). This embodiment is considered particularly useful when the first application does not alleviate the symptoms of the condition being treated.

In certain embodiments the present invention is directed to a topical formulation of a therapeutically effective amount of an active agent(s) as described herein. Preferably the topical formulation is applied to a predetermined area of skin to deliver a therapeutically effective amount of an active agent(s) to a human.

In certain embodiments the present invention is directed to a topical formulation for treating migraines and/or cluster headaches, muscle sprains, muscle spasms, spasticity, tension headaches, tension related migraines and related conditions associated with muscle tension and pain comprising a therapeutically effective amount of an active agent(s) incorporated into a pharmaceutically acceptable excipient for topical administration onto the skin of a human patient, wherein the therapeutically effective amount of active agent(s) being selected from the group consisting of: i) an ergot alkaloid; ii) a skeletal muscle relaxant; or iii) a combination of an ergot alkaloid and a skeletal muscle relaxant; the active agent being present in an effective concentration in the excipient such that a unit dose of the topical formulation, when applied to an affected area of a human patient, provides relief from migraines or cluster headaches, muscle sprains, muscle spasms, spasticity, tension headaches, tension related migraines and related condition within about 2 hours after topical administration to the human patient.

In certain embodiments, the present invention is directed to a unit dose of a therapeutically effective amount of an active agent(s) for topical administration and delivery of the active agent(s) to a human in need of treatment thereof.

In certain embodiments, the present invention is directed to a unit dose of a topical formulation for treating migraines and/or cluster headaches, muscle sprains, muscle spasms, spasticity, tension headaches, tension-related migraines and related conditions associated with muscle tension and pain comprising a therapeutically effective amount of an active agent(s); and a pharmaceutically acceptable excipient; the unit dose providing pain relief in at least 50 percent of a population of patients experiencing migraines and/or cluster headaches, muscle sprains, muscle spasms, spasticity, tension headaches, tension-related migraines and related conditions associated with muscle tension and pain in a time period within about 2 hours after application of the unit dose to a region of skin of a human in need of treatment thereof.

In other embodiments, the active agent(s) is in a transdermal therapeutic system. Preferably transdermal therapeutic system is applied to a predetermined area of skin to deliver a therapeutically effective amount of an active agent(s) to a human.

In certain other embodiments, the present invention is directed to a metered dose device comprising: a) multiple unit doses of a topical formulation, wherein each unit dose comprises a therapeutically effective amount of an active agent(s) incorporated into a pharmaceutically acceptable excipient for topical administration onto the skin of a human patient, the therapeutically effective amount of active agent(s) being selected from the group consisting of: i) an ergot alkaloid; ii) a skeletal muscle relaxant; or iii) a combination of an ergot alkaloid and a skeletal muscle relaxant; and b) an actuator capable of being actuated to dispense single unit doses from the device; each unit dose providing the active agent(s) in a form which is immediately absorbable when the unit dose is applied onto human skin, the unit dose providing relief from migraines or cluster headaches, muscle sprains, muscle spasms, spasticity, tension headaches, tension related migraines and related conditions associated with muscle tension and pain within about 2 hours after topical administration to the patient. Preferably the metered dose device provides multiple unit doses of the topical preparation. Certain metered dose devices include, for example and without limitation, a syringe without a needle (e.g., a tuberculin syringe without needle, a dropper, a metered dose spray device, metered tube, and the like. Preferably the metered dose device includes an actuator capable of being actuated to dispense single unit doses comprising the ergot alkaloid from the device.

In certain preferred embodiments, the formulations of the present invention are designed to provide a therapeutically effective dose of the active agent(s) at the application site, for rapid local absorption. Most preferably the formulations of the present invention are immediate releasing formulations, such that a therapeutically effective amount of the active agent(s) is available for rapid absorption. The formulations of the present invention preferably are suitable for the treatment of acute migraine attacks and/or cluster headaches, muscle sprains, muscle spasms, spasticity, tension headaches, tension-related migraines and related conditions associated with muscle tension and pain.

In certain embodiments the active agent(s) formulations described herein are preferably applied to the posterior cervical region of a human experiencing or about to experience a migraine and/or cluster headache. In certain preferred embodiments, the active agent(s) formulations are applied to the back of the neck, preferably in close proximity to or on the area of skin above the brain stem.

In certain embodiments the active agent(s) formulations described herein are preferably applied to a region of skin of a human experiencing or about to experience muscle sprains, muscle spasms, spasticity, tension headaches, tension-related migraines and related conditions associated with muscle tension and pain. In certain preferred embodiments, the active agent(s) formulations are applied to the extremities, the torso or the back of the neck, preferably in close proximity to or on the area of skin experiencing the muscle sprain, muscle spasm, spasticity tension headache, tension-related migraines and related conditions associated with muscle tension and pain.

In certain other embodiments, the formulations described herein are fast acting. For example, the symptoms associated with migraine and/or cluster headache, muscle sprain, muscle spasm, spasticity, tension related headache, tension related migraine and related conditions associated with muscle tension and pain are relieved within about 2 hours, preferably within about 5 minutes to about 2 hours, within about 5 minutes to about 1 hour and most preferably within about 5 minutes to about 30 minutes after application of the formulation. In certain preferred embodiments, the formulations of the present invention provide relief from migraine and/or cluster headache, muscle sprain, muscle spasm, spasticity, tension related headache, tension related migraine and related conditions associated with muscle tension and pain within from less than 1 minute to about 2 hours, from about 1 minute to about 2 hours, and most preferably from about 1 minute to about 15 minutes.

In certain preferred embodiments, the active agent(s) is included in a topical formulation further comprising one or more pharmaceutically acceptable excipients that aid in the absorption of the active agent(s) when a unit dose of the formulation is applied topically to the headache region of the human patient.

In certain embodiments of the present invention, when a therapeutically effective amount an active agent(s) is utilized for the treatment of migraines and/or cluster headache, the active agent(s) is selected from the group consisting of an ergot alkaloid, a serotonin agonist or any pharmaceutically acceptable base, salts or combinations thereof. In certain other embodiments, the topical formulations comprising an ergot alkaloid and/or a serotonin agonist further comprise one or more additional active agent(s) incorporated therein.

In certain embodiments, the present invention provides a topical formulation for treating a migraine or cluster headache comprising a serotonin agonist and one or more additional active agent(s) incorporated into a pharmaceutically acceptable vehicle for topical administration onto the skin of a human patient; the formulation provides the serotonin agonist and the additional active agent(s) in a form which is immediately absorbable when the formulation is applied onto human skin; the serotonin agonist comprising from about 0.5 to about 200 mg of sumatriptan, by weight based on the succinate salt; and the formulation provides relief from a migraine or cluster headache within about 2 hours after topical administration to a human patient.

In certain embodiments, the present invention provides a topical formulation for treating muscle sprains, muscle spasms, spasticity, tension headaches, tension related migraines and related conditions associated with muscle tension and pain comprising a therapeutically effective amount of a serotonin agonist together with a therapeutically effective amount of a muscle relaxant (e.g., tizanidine) in a pharmaceutically acceptable vehicle for topical administration such that the formulation provides pain relief in at least 50 percent of a population of patients experiencing muscle sprains, muscle spasms, spasticity, tension headaches, tension related migraines and related conditions associated with muscle tension and pain, in a time period within about 2 hours after application of the unit dose to the affected area.

In certain preferred embodiments, the present invention provides a a topical formulation for the acute treatment of migraine comprising about 0.5 to about 200 mg of sumatriptan succinate agonist and one or more additional active agent(s) incorporated into a pharmaceutically acceptable topical carrier; the topical preparation provides for the immediate availability of an effective amount of the sumatriptan and the additional active agent(s) for absorption when the unit dose is applied to a headache region of a human patient. In certain preferred embodiments, the additional active agent(s) may comprise a therapeutically effective amount of an ergot alkaloid (e.g., dihydroergotamine); a muscle relaxant (e.g., tizanidine); or combinations thereof. In certain embodiments, a therapeutically effective amount of the ergot alkaloid may replace the triptan in the formulation, and is combined with a therapeutically effective amount of the muscle relaxant in the formulation.

In certain preferred embodiments, the present invention provides a topical formulation for the acute treatment of migraine comprising from about 0.5 to about 200 mg of sumatriptan succinate and one or more additional active agent(s) incorporated into a pharmaceutically acceptable topical carrier; the topical formulation provides for the immediate delivery of an effective amount of the sumatriptan succinate and the additional active agent(s) through the skin of the posterior cervical area of a human patient to achieve relief from a migraine or cluster headache within about 2 hours after topical application of the topical formulation.

In certain embodiments of the present invention, when a therapeutically effective amount an active agent(s) is utilized for the treatment of muscle sprains, muscle spasms, spasticity, tension headache, tension related migraine or related condition associated with muscle tension and pain, the active agent(s) is a skeletal muscle relaxant or any pharmaceutically acceptable base, salt or combination thereof.

In certain embodiments, the present invention is directed a topical formulation for treating muscle spasms, muscle sprains, spasticity, tension headache, tension-related migraines and related conditions associated with muscle tension and pain comprising a skeletal muscle relaxant together with at least one pharmaceutically acceptable excipient for topical application, the formulation including the skeletal muscle relaxant in an effective concentration such that a therapeutically effective dose of the skeletal muscle relaxant is absorbed at the site of application on the skin of a human patient in proximity to an area to be treated, wherein the formulation providing a therapeutic effect within less than about 15 minutes after topical administration to the skin of a human patient.

In certain embodiments, the present invention is directed a topical formulation for treating muscle spasms, muscle sprains, spasticity, tension headache, tension-related migraines and related conditions associated with muscle tension and pain comprising a skeletal muscle relaxant together and one or more additional therapeutically active agent(s). In certain preferred embodiments the skeletal muscle relaxant is tizanindine.

In certain embodiments, the present invention is directed to a topical formulation for the treatment of muscle spasms, muscle sprains, spasticity, tension headache, tension-related migraines and related conditions associated with muscle tension and pain comprising a dose of tizanidine in an amount from about 0.2 mg to about 4 mg, said dose being effective to provide a therapeutic localized effect when the dose of the tizanidine is applied to the skin of a human patient, the dose of tizanidine being sub-therapeutic for providing a systemic effect; and at least one pharmaceutically acceptable excipient for topical application.

In certain embodiments, the present invention is further directed to a method of manufacturing the formulations described herein.

In certain embodiments, the present invention is further directed to the use of one of the active agents disclosed herein in the treatment of migraines and/or cluster headaches, muscle sprains, muscle spasms, spasticity, tension headaches, tension related migraines and related conditions associated with muscle tension and pain.

In certain embodiments, the present invention is further directed to the use of one of the active agents disclosed herein in the preparation of a topical medicament for the treatment of migraines and/or cluster headaches, muscle sprains, muscle spasms, spasticity, tension headaches, tension related migraines and related conditions associated with muscle tension and pain.

In certain other embodiments, the present invention is directed to the use of an active agent in the preparation of a topical formulation for treating migraines or cluster headaches, muscle sprains, muscle spasms, spasticity, tension headaches, tension related migraines and related conditions associated with muscle tension and pain comprising incorporating a therapeutically effective amount of an active agent(s) into a pharmaceutically acceptable excipient for topical administration onto the skin of a human patient; the therapeutically effective amount of active agent(s) being selected from the group consisting of: i) an ergot alkaloid; ii) a skeletal muscle relaxant; or iii) a combination of an ergot alkaloid and a skeletal muscle relaxant; the active agent being present in an effective concentration in the excipient such that a unit dose of the topical formulation, when applied to an affected area of a human patient, provides relief from migraines or cluster headaches, muscle sprains, muscle spasms, spasticity, tension headaches, tension related migraines and related condition within about 2 hours after topical administration to the human patient.

For purposes of the present invention, the term "active agent" includes ergot alkaloids, serotonin agonists, skeletal muscle relaxants and any pharmaceutically acceptable salts, prodrugs, derivatives and combinations thereof.

For purposes of the present invention, the term "related conditions associated with muscle tension and pain" includes, but is not limited to myopathies, channnelopathies, myotonic dystrophy, myotonia congenita, familial periodic paralysis, centronuclear myopathy, dermatomyositis, polymyositis, inclusion body myositis, muscular dystrophy, and the like.

For purposes of the present invention, a "topical formulation" includes, liquids, semisolids or solid formulations. Liquids include, for example, solutions in the form of drops, tinctures, sprays, suspensions, lotions, emulsions and dispersions; semisolids include, for example, ointments, creams, foams, pastes, gels; an solids include, for example, powders, granulates, pellets and microcapsules, all of which releases one or more drugs at a predetermined rate over a defined period of time to a defined site of application.

For purposes of the present invention, a "transdermal therapeutic system" is defined as a drug-containing device (including e.g., patch, disc, etc.) which releases one or more drugs at a predetermined rate over a defined period of time to a defined site of application.

For purposes of the present invention, a "topical formulation" includes, for example, ointments, creams, lotions, pastes, gels, etc., which releases one or more drugs at a predetermined rate over a defined period of time to a defined site of application.

For purposes of the present invention, "transdermal" delivery is the delivery by passage of a drug through the skin and into the bloodstream.

For purposes of the present invention the term "immediate release" means that the ergot alkaloid is available for immediate absorption (e.g., available within 0 to about 5 minutes) upon application of the formulation. This is in contrast to a delayed or prolonged absorption which typically results from, e.g., a transdermal therapeutic device).

For purposes of the present invention "therapeutically effective" or "effective" amount is meant to be a nontoxic but sufficient amount of a compound to provide the desired therapeutic effect, e.g., avoidance of the onset of a migraine and or increased alleviation of the migraine and/or cluster headache. In the present case, for example, it is the dose of ergot alkaloid which will be effective in relieving symptoms of the migraine or cluster headache. An "effective" amount of a permeation enhancer as used herein, for example, means an amount that will provide the desired increase in skin permeability and, correspondingly, the desired depth of penetration, rate of administration, and amount of drug to be delivered.

For purposes of the present invention, the term "delivers" when used with respect to the topical formulation or transdermal therapeutic system means that the formulation or system provides a mean relative release rate or flux of the drug out of the formulation or system and through the skin of the patient.

For purposes of the present invention, the term "co-administration" means either the administration of a single composition containing an active agent(s) and the one or more additional active agent(s), or the administration of an active agent and the one or more additional active agent(s) as separate compositions contemporaneously therewith or within short enough time periods that the effective result is equivalent to that obtained when both compounds are administered as a single composition.

By "predetermined area of skin" is intended a defined area of intact unbroken living skin. In certain embodiments of the present invention, the predetermined area will be in the range of about 1 cm$^2$ to about 100 cm$^2$, preferably in the range of about 10 cm$^2$ to about 100 cm$^2$, more preferably in the range of about 20 cm$^2$ to about 60 cm$^2$. However, it will be appreciated by those skilled in the art of topical delivery that the area of skin through which drug is administered may vary significantly, depending on the formulation, dose, the application of the formulation, and the like.

"Penetration enhancement" or "permeation enhancement" for purposes of the present invention relates to an increase in the permeability of skin to a pharmacologically active agent(s), i.e., so as to increase the rate at which the drug permeates through the skin and enters the bloodstream. The enhanced permeation effected through the use of such enhancers can be observed by measuring the rate of diffusion of drug through animal or human skin using a diffusion cell apparatus.

For purposes of the present invention, the "headache region" is defined as the skin region of the head and/or neck above which a patient feels a migraine or cluster headache pain is occurring or is imminent. Typically the headache region includes, for example, the frontotemporal region and/or upper posterior cervical area on the side of the headache. Preferably the headache region includes the post cervical area in close proximity to the brain stem. Preferably this area is a relatively hairless area of the patient's head and/or neck.

For purposes of the present invention, the region experiencing muscle sprains, muscle spasms, spasticity, tension headache, tension-related migraines or other related conditions associated with muscle tension and pain is defined as the skin region of the upper and lower torso where a patient experiences a muscle tension or pain. Typically the region experiencing muscle tension or pain includes, for example, the abdomen, back, chest, arms, legs, and head. Preferably, when experiencing a tension headache or tension-related migraines, the region includes the frontotemporal region and/or upper posterior cervical area. More preferably the tension headache or tension-related migraine region includes the post cervical area in close proximity to the brain stem. Preferably this area is a relatively hairless area of the patient's head and/or neck of the patient. In certain circumstances, when patients present with classic migraine symptoms, e.g., nausea, vomiting, blurred vision, throbbing headache, with or without complaints of neck pain or spasm, application of the formulations described herein to the post cervical or frontotemporal regions may also result in alleviation of migraine symptoms.

DETAILED DESCRIPTION

Sickness and vomiting typically occurring in migraine make oral administration of the active agent(s) for migraine treatment difficult. Therefore, topical administration of an active agent(s) may offer considerable advantages.

Certain other advantages of topical administration may include increased efficiency by avoiding the first-pass effect of the liver, avoiding discomfort and risks of an intravenous treatment, avoiding side effects in the region of the gastrointestinal tract in the case of oral medication, and good patient acceptance. Absorption peaks involving the risk of systemic side effects may also be avoided.

Typically the site of administration of transdermal delivery systems have been selected at various locations such as on the chest, on the arm, or on the thigh for various reasons such as desired skin permeability to an agent(s), convenience or cosmetic reasons. According to the present invention the topical formulation is preferably applied to an affected area experiencing migraine or cluster headache, muscle sprain, muscle spasm, spasticity, tension headache, tension related migraine and related conditions associated with muscle tension and pain. The local (e.g., regional) and systemic administration of agent(s) to the area and in certain embodiments results in lower serum levels necessary to provide a therapeutic effect than that reported in the prior art.

The methods and the formulations described herein allow for the migraines and/or cluster headaches, muscle sprains, muscle spasms, spasticity, tension headache, tension-related migraines or other related conditions associated with muscle tension or pain to be treated much faster and more effectively than such prior art modes of administration. For example, when a patient experiencing a migraine or cluster headache, or who perceives that such headache is imminent, or when a patient experiences a muscle sprain, muscle spasm, spasticity, tension headache, tension related migraine or related condition associated with muscle tension or pain, it is contemplated that the patient can apply a dose of active agent(s) to the affected area of the skin and experience relief within, e.g., less than about 15 minutes, preferably within less than about 15 minutes to several days, within less than about 15 minutes to about 3 days, less than about 15 minutes to about 24 hours. In a most preferred embodiment, relief is experienced within from less than about 15 minutes to about 2 hours, from less than about 15 minutes to about 1 hour, or from less than about 15 minutes to about 30 minutes after application of the active agent(s). The method of the invention further contemplates that if the dose does not completely alleviate the symptoms, applying a second dose within about 3 hours, preferably within about 15 minutes to about 3 hours, within about 15 minutes to about 2 hours, and most preferably within about 15 minutes to about 1 hour after the first application.

By the methods of the present invention, a substantial percentage of patients may experience relief within a relatively short period of time after application. For example, more than 50 percent of the patients may experience pain relief or relief of symptoms within one hour of the application of the dose of active agent(s) to the affected region. In certain preferred embodiments, more than 70 percent, preferably more than 80 percent, and most preferably more than 90% of the patients may experience pain relief or relief of symptoms.

In certain embodiments of the present invention, the method of treating a human patient suffering from migraine or cluster headache, muscle sprain, muscle spasms, spasticity, tension headache, tension related migraines or other related conditions associated with muscle tension or pain comprises applying a topical formulation which comprises an active agent(s), as described herein, to the affected region, such that the topical formulation delivers an amount of active agent(s) which is therapeutically effective. Preferably the topical formulation contains a unit dose of the active agent(s) that provides relief of a migraine and/or cluster headache, muscle sprain, muscle spasms, spasticity, tension headache, tension related migraines or other related conditions associated with muscle tension or pain. In certain embodiments, the present invention provides a method of treating an imminent attack, e.g., migraine attack or muscle spasm, in a patient comprising topically administering an active agent(s) to the patient in need of such treatment.

The methods of the present invention may also, if desired, involve pre-treatment of the skin with an enhancer to increase the permeability of the skin to the applied drug. The methods of the present invention may include pre-treatment or "prepping" of the skin area with a substance that opens up the skin pores. Additionally, the methods of the present invention may include, if desired, pre-treatment or "prepping" of the skin with an alcohol swab or the like to rid the area of dirt, make-up, oil, and the like, prior to application of the drug.

Preferably, the topical formulation is applied to a predetermined area of skin to deliver the active agent(s) to a human.

In certain embodiments, the topical formulation of the present invention comprises an active agent(s) in an amount which is therapeutically effective when administered topically to the affected area of a humans patient, but which provides a plasma concentration which is subtherapeutic if orally administered.

In certain embodiments, by applying the formulation of the present invention comprising a dose of active agent(s) at the affected area, e.g., headache region of a migraine or cluster headache, it may be possible for the use of lower doses of drug for faster relief of the headache than if applied to the trunk or limbs of a human patient, and the lower plasma levels of drug which result from lower doses may thereby reduce unwanted side effects of the active agent(s). For purposes of the present invention, the "trunk" of a human is the body of a human excluding the head, neck and limbs.

In certain preferred embodiments, the methods of the present invention further include a method of treating a human patient suffering from migraine and/or cluster headache, muscle sprain, muscle spasms, spasticity, tension headache, tension related migraines or other related conditions associated with muscle tension or pain comprising applying a topical formulation, or transdermal therapeutic system, comprising an active agent(s), a pharmaceutically acceptable salt thereof, derivative thereof, active metabolite thereof or prodrug thereof to the affected region of the patient, the active agent(s) is in the formulation in an amount of from about 0.001% to about 99.9%, preferably from about 0.1% to about 10% and more preferably from about 1% to about 5%.

The total dose of the active agent(s) contained in the formulation will be a dose that is suitable for application of a unit dose of the formulation on the skin of a human patient at the affected region such that an effective amount of the active agent(s) is absorbed within the requisite period of time to provide the therapeutic effect described herein.

In certain preferred embodiments, the formulations of the present invention contain the active agent(s) is in the form of a base, pharmaceutically acceptable salt thereof, active metabolite thereof, or prodrug thereof.

The total amount of the active agent(s) that constitutes a therapeutically effective amount may vary according to the type of active agent(s) utilized, the severity of the condition, the variability of the responsiveness of a particular patient, desired duration of treatment, the surface area of the skin over which the formulation or device is to be placed, and the inclusion/exclusion of excipients in the formulation or device. Accordingly it is not practical to enumerate particular preferred amounts but such can be readily determined by those skilled in the art with due consideration of these factors.

In certain embodiments of the present invention, the active agent(s) is in a topical administration form (e.g., a topical formulation) drops, tinctures, sprays, suspensions, lotions, emulsions dispersions, ointments, creams, foams, pastes, gels, powders, granulates, pellets and microcapsules or the like.

A topical formulation containing an active agent(s) in accordance with this invention may be used to treat any condition capable of treatment with active agent(s), e.g., migraine headaches and cluster headaches. The topical formulation can be placed on the skin surrounding the headache region and allowed to remain for a time sufficient to achieve or maintain the intended therapeutic effect.

In certain embodiments of the present invention, the active agent(s) is an ergot alkaloid. The ergot alkaloids are derivatives of the tetracyclic compound 6 methylergoline. Ergot alkaloids exist naturally, however, several semisynthetic ergot alkaloids have been produced. Ergot alkaloids are structurally related in that they all contain an indole ring system. Three main groups of ergoline, or ergot alkaloids exist. These groups include the clavine type, the water soluble lysergic acid type and the water-insoluble lysergic acid type or peptide ergot alkaloids.

The clavinet type alkaloids are precursors to the other ergot alkaloids and are generally not used pharmacologically. However, agroclavine, a clavinet type alkaloid, has been used as a uterine stimulant. The water-soluble lysergic acid derivatives are primarily amide derivatives and include, for example, ergonovine and methysergide. The water-insoluble lysergic acid derivatives are primarily peptide ergot alkaloids, e.g., ergotamine.

The ergot alkaloids useful in the present invention, are those which are pharmaceutically acceptable and provide a therapeutic effect in the treatment of migraine or cluster headaches, including, for example and without limitation, bromocriptine, ergocristine, ergocristinine, ergotamine, ergotaminine, ergocryptine, ergocryptinine, ergocornine, ergocorninine, ergosine, ergosinine, ergonovine, ergometrinine, dihydroergotamine, lisuride, d-lysergic acid, d-isolysergic acid, lysergol, lergotrile, metergoline, methysergide, methylergonovine pharmaceutically acceptable salts thereof, mixtures thereof, and derivatives thereof. Preferably the ergot alkaloid is ergotamine, dihydroergotamine, methysergide, salts, derivatives, active metabolites or prodrugs thereof e.g., dihydroergotamine mesylate. As used herein, the identification of an agent(s) to be delivered includes not only the ergot alkaloid per se but also its topically administrable prodrugs, active metabolites and prodrugs of the active metabolites.

Ergotamine was first manufactured in 1921 by Sandoz (now Novartis) under the trade name Gynergen and was marketed for gynecological use. Controlled studies in the 1930s proved ergotamine to be effective for migraine. Hart, Carol, "Drugs for Migraine", Modern Drug Discovery, 1999 2(2), 20-21, 23-24, 28, 31. Today ergotamine is available as 2 mg sublingual tablets under the trade names Ergostat and Ergomar. Ergotamine is also available in combination with caffeine under the trade names Wigraine (1 mg ergotamine/100 mg caffeine as a tablet) and Caffergot (1 mg ergotamine/100 mg caffeine as a suppository).

Ergotamine exerts partial agonist and antagonist activity at tryptominergic, dopaminergic and alpha-adrenergic receptors. Ergotamine reduces extracranial blood flow, which causes a decline in the amplitude of pulsation in the cranial arteries and decreases hyperperfusion of the basilar artery territory. Ergotamine stimulates the chemoreceptor trigger zone and, therefore, is known for producing emesis.

Dihydroergotamine is available as a 1 mg/ml injection under the trade name D.H.E. 45. Dihydroergotamine differs from ergotamine in its degree of activity. Dihydroergotamine is a hydrogenated derivative of ergotamine that possesses less vasoconstrictive action than ergotamine and is about 12 times less active as an emetic. Suitable salts of dihydroergotamine, include, but are not limited to hydrochloride, methanesulfonate, ethanesulfonate, tartarate, maleate, succinate and mesylate. The active metabolites 8'-hydroxydihydroergptamine or 8',10'-dihydroxydihydroergotamine may be used alone or together with dihydroergotamine in the formulations of the present invention. The prodrug, dihydroergotamine dimethanolate may also be used alone or in combination with dihydroergotamine in the formulations of the present invention.

Methysergide is a semisynthetic ergot derivative and is marketed as 2 mg tablets under the trade name Sansert (Novartis). Methysergide's mechanism of action is unknown. However, it does not possess intrinsic vasoconstrictive properties. It is believed that methysergide inhibits or blocks the effects of serotonin, which is said to be a known substance involved with vascular headaches. Accordingly, methysergide administration is indicated in the prophylaxis, preventative treatment, or reduction of intensity and frequency of vascular headaches.

The dose of ergot alkaloid utilized in the present invention ranges from about 0.1 mg to about 10 mg, preferably from about 0.5 mg to about 6 mg.

The synthesis of certain ergot alkaloids of the present invention can be carried out according to U.S. Pat. No. 4,491,664 (Oppolzer, Wolfgang) the disclosures of which are hereby incorporated by reference.

In certain other embodiments, the active agent(s) is a serotonin agonist. The serotonin agonists for use in the present invention, include, for example and without limitation, buspirone, dihydroergotamine, eltoprazine, ergotamine, flesinoxan, ipsapirone, lesopitron, methysergide, repinotan, tandospirone, tegaserod, xaliproden and pharmaceutically acceptable salts thereof, mixtures thereof, and derivatives thereof. Preferably the serotonin agonist includes sumatriptan, naratriptan, eletriptan, rizatriptan, zolmitriptan, almotriptan, frovatriptan, pharmaceutically acceptable salts thereof, mixtures thereof, and derivatives thereof. Preferably the serotonin agonist is sumatriptan (3-(2-(dimethylamino) ethyl)-N-methyl-1H-indole-5-methanesulfonamide), one of its salts or derivatives. As used herein, the identification of an agent(s) to be delivered includes not only the serotonin agonist per se but also its topically administrable prodrugs, active metabolites and prodrugs of the active metabolites.

In certain preferred embodiments, the formulations of the present invention contain sumatriptan base or a pharmaceutically acceptable salt thereof (e.g., sumatriptan succinate) as the serotonin agonist. When the serotonin agonist is sumatriptan or a pharmaceutically acceptable salt thereof, the amount of sumatriptan is in an amount of from about 0.5 mg to about 200 mg, preferably in an amount of from about 5 mg to about 200 mg, from about 5 mg to about 100 mg, from about 5 mg to about 50 mg, or from about 5 mg to about 25 mg, and most preferably is in an amount of 12.5 mg, 25 mg, 50 mg or 100 mg.

Comparative oral doses of certain triptans are as follows: sumatriptan, 50 mg; rizatriptan, 10 mg; naratriptan, 2.5 mg; zolmitriptan, 2.5 mg; and eletriptan, 40 to 80 mg. Therefore, one skilled in the art can readily determine therapeutically equivalent doses of serotonin agonists that may be useful in the present invention. However, it is noted that the differences in oral doses may not directly correspond to the differences in doses that are therapeutically effective via transdermal delivery of the serotonin agonist. Factors such as metabolism of the serotonin agonist, the ability of the drug to pass through the skin, among others, may affect the amount of serotonin agonist necessary to provide a therapeutic effect. One skilled in the art would readily understand this and adjust for the same.

A topical formulation containing a serotonin-agonist in accordance with this invention may be used to treat any condition capable of treatment with serotonin agonists, e.g., migraine headaches and cluster headaches. The topical formulation can be placed on the skin surrounding the headache region and allowed to remain for a time sufficient to achieve or maintain the intended therapeutic effect.

In certain embodiments, the active agent(s) is a skeletal muscle relaxant. The skeletal muscle relaxants for use in the present invention include centrally acting skeletal muscle relaxants, direct acting skeletal muscle relaxants and any combinations or mixtures thereof.

Centrally acting skeletal muscle relaxants include, but are not limited to for example and without limitation, afloqulone, baclofen, botulin toxins, carisoprodol, chlormezanone, chlorphenesin carbamate, chlorzoxazone, cyclobenzaprine, clonazepam, diazepam, eperisone, idrocilamide, inaperisone, mephenesin, mephenoxalone, methocarbamol, metaxalone, mivacurium chloride, orphenadrine, phenprobamate, pridinol mesylate, quinine, tetrazepam, thiocolchicoside, tizanidine, tolperisone, pharmaceutically acceptable salts thereof, active metabolites thereof, prodrugs thereof and mixtures thereof. Preferably the skeletal muscle relaxant is tizanidine base, tizanidine hydrochloride or any pharmaceutically acceptable salts thereof, prodrugs thereof or mixtures thereof.

Direct acting skeletal muscle relaxants include dantrolene.

Tizanidine is a centrally acting $\alpha_2$-adrenergic agonist. Tizanidine possesses an imidizole structure similar to that of clonidine (anti-hypertensive) and other $\alpha_2$-adrenergic agonists. Tizanidine is completely absorbed after oral administration with its peak effect occurring within about 1 to about 2 hours. The mechanism of action of tizanidine is related to its presumed ability to increase presynaptic inhibition of motor neurons thereby reducing spasticity with its greatest effect asserted on polysynaptic pathways.

In certain other embodiments, the anticonvulsant drug tiagibine can be used in place of or in combination with the skeletal muscle relaxant.

The total dose of the skeletal muscle relaxant contained in the formulation is preferably a dose that is suitable for application of a unit dose of the formulation on the skin of a human patient at the region experiencing muscle sprains, muscle spasms, spasticity, tension headache, tension-related migraines or other related conditions associated with muscle tension and pain such that an effective amount of the skeletal muscle relaxant is topically absorbed within a requisite period of time to provide a therapeutic effect described herein.

In certain preferred embodiments, the formulations of the present invention contain a skeletal muscle relaxant base, pharmaceutically acceptable salt thereof, active metabolite thereof, or pro-drug thereof (e.g., tizanidine hydrochloride) as the skeletal muscle relaxant. When the skeletal muscle relaxant is tizanidine or pharmaceutically acceptable salt thereof, active metabolite thereof, or prodrug thereof, the amount of tizanidine present in the formulation is in a range from about 0.25 mg to about 2 mg, and preferably from about 0.4 mg to about 0.8 mg. In certain other preferred embodiments the amount of tizanidine included in a topical unit dose formulation is from about 0.2 mg to about 4 mg.

For comparative purposes, prior art topical doses of skeletal muscle relaxants range from about 10 mg to about 50 mg which is more than 10 to 100 times greater than the dosage range for the skeletal muscle relaxants of the present invention.

In addition, oral doses of certain skeletal muscle relaxants are as follows: carisoprodol 350 mg; chlorphenesin 400 mg; chlorzoxazone 250 mg; cyclobenzaprine 10 mg; metaxalone 800 mg; methocarbamol 1 gm to 1.5 gm; tizanidine 4 mg; orphenadrine 100 mg; diazepam 2 mg to 10 mg; baclofen 5 mg to 20 mg; and dantrolene 25 mg to 100 mg. Therefore, one skilled in the art can readily determine therapeutically equivalent doses of skeletal muscle relaxants that may be useful in the present invention. However, it is noted that the differences in oral doses may not directly correspond to the differences in doses that are therapeutically effective via transdermal delivery of the skeletal muscle relaxant. Factors such as metabolism of the skeletal muscle relaxant, the ability of the drug to pass through the skin, among others, may affect the amount of skeletal muscle relaxant necessary to provide a therapeutic effect. One skilled in the art would readily understand this and adjust for the same.

In certain other embodiments, in addition to the ergot alkaloids, serotonin agonists and skeletal muscle relaxants, the topical formulation or transdermal therapeutic system may further comprise another active agent(s) in combination with the ergot alkaloids, serotonin agonists and skeletal muscle relaxants, e.g., analgesics, antimimetics, psychopharmacologic agent(s), or sedatives. In certain other embodiments, when one or more of the additional active agents are contemplated, each additional active agent may be incorporated into the same topical formulation or incorporated into separate topical formulations or transdermal therapeutic systems and co-administered to a predetermined area of skin.

The topical formulations of the present invention (e.g., ointment, gel, cream, or the like), must be suitable for topical administration of a drug, i.e., must contain pharmaceutically acceptable excipients compatible with application to the skin tissue. In certain embodiments, in addition to the active agent(s), the topical formulations and/or transdermal therapeutic systems of the present invention may include at least one excipient such as a penetration enhancer, anti-oxidant, stabilizer, or carrier. Additionally or alternatively, the present invention may include the application of electric current (iontophoresis) for enhancing permeation of the active agent(s).

In certain embodiments of the present invention, wherein the topical formulation further includes a permeation enhancer composition, the amount of enhancer composition present in the formulation will depend on a number of factors, e.g., the strength of the particular enhancer composition, the desired increase in skin permeability, and the amount of active agent(s) which is necessary to deliver.

In certain embodiments, the topical formulations comprising a active agent(s) in an ointment, gel, cream or the like, will typically contain on the order of about 0.001 to about 99% by weight, preferably 0.01% to 10% by weight active agent(s), and about 0.1% to about 50% by weight, preferably from about 1% to about 30% by weight of a permeation enhancer composition, with the remainder of the composition comprising an excipient.

Suitable permeation enhancers include, but are not limited to, dimethylsulfoxide (DMSO), N,N-dimethylacetamide (DMA), decylmethylsulfoxide ($C_{10}$ MSO), polyethylene glycol monolaurate (PEGML), propylene glycol (PG), PGML, glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil as described in U.S. Pat. No. 5,229,130 to Sharma. Such oils include, for example, safflower oil, cotton seed oil and corn oil.

Additional permeation enhancers for use in conjunction with the present invention are lipophilic compounds having the formula $[RCOO]_n R'$, wherein n is 1 or 2 and R is $C_1$-$C_{16}$ alkyl optionally substituted with 1 or 2 hydroxyl groups, and R' is hydrogen or $C_1$-$C_{16}$ alkyl optionally substituted with 1 or 2 hydroxyl groups. Within this group, a first subset of compounds are represented by the formula $[CH_3(CH_2)_m COO]_n$·R' in which m is an integer in the range of 8 to 16, n is 1 or 2, and R' is a lower alkyl ($C_1$-$C_3$) residue that is either unsubstituted or substituted with one or two hydroxyl groups. Preferred enhancers within this group include an ester which is a lower alkyl ($C_1$-$C_3$) laurate (i.e., m is 10 and n is 1) such as "PGML". It will be appreciated by those skilled in the art that the commercially available material sold as "PGML" is typically although not necessarily a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. Also within this group is a second subset of compounds, namely, esters of fatty alcohols represented by the formula $CH_3(CH_2)_m$—O—CO—$CHR_1R_2$, in which $R_1$ and $R_2$ are independently hydrogen, hydroxyl, or lower alkyl ($C_1$-$C_3$), and m is as above. Particularly preferred enhancers within this group are lauryl lactate and myristyl lactate. In addition, a third subset of compounds within this group is analogous fatty acids, i.e., acids having the structural formula $CH_3(CH_2)_m COOH$ where m is as above. A particularly preferred acid is lauric acid.

Other enhancer compositions are wherein a lipophilic compound as just described, particularly PGML is combined with a hydrophilic compound, such as a $C_2$-$C_6$ alkanediol. One preferred hydrophilic enhancer within this group is 1,3-butanediol. Such enhancer compositions are described in detail in PCT Publication No. WO 95/05137, published Feb. 23, 1995, herein incorporated by reference. Another hydrophilic enhancer that may be included in these compositions is an ether selected from the group consisting of diethylene glycol monoethyl ether (Transcutol®) and diethylene glycol monomethyl ether. Such enhancer compositions are described in detail in U.S. Pat. Nos. 5,053,227 and 5,059,426 to Chiang et al., the disclosures of which are herein incorporated by reference.

Other enhancer compositions may include mixture or combinations of any of the aforementioned enhancers, and the like.

In certain embodiments of the present invention, the formulation of the present invention, further comprises one or more ingredients selected from the group consisting of ethoxydiglycol, water, glycerine, $C_{12-15}$alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), *prunus amygadalus amara* (bitter almond) kernel oil, *vitis vinifera* (grape) seed extract, *triticum vulgare* (wheat) germ oil, retinyl palmitate (vitamin A palmitate), ascorbyl palmitate (vitamin C palmitate), prolipo multi-emulsion liposomic system, tetrasodium EDTA, phenoxyethanol, and sodium hydroxymethylglycinate.

In certain embodiments the topical formulation may include at least one water-insoluble, pharmacologically approved, alkyl cellulose or hydroxyalkyl cellulose, and the like. Alkyl cellulose or hydroxyalkyl cellulose polymers for use in this invention include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent(s) may be used to modify the polymer's characteristics. For example, esters such as dibutyl or diethyl phthalate, amides such as diethyldiphenyl urea, vegetable oils, fatty acids and alcohols such as acid oleic and myristyl may be used in combination with the cellulose derivative.

In certain embodiments, the topical formulation may further include hydrocarbons such as liquid paraffin, vaseline, solid paraffin, microcrystalline wax, etc.; higher aliphatic alcohols such as cetyl alcohol, hexadecyl, alcohol, stearyl alcohol, oleyl alcohol, etc.; esters of higher fatty acids with higher alcohols such as beeswax, etc.; esters of higher fatty acids with lower alcohols such as isopropyl myristate, isopropyl palmitate, etc.; vegetable oils, modified vegetable oils, hydrous lanolin and its derivative, squalene, squalane; higher fatty acids such as palmitic acid, stearic acid, etc. and the like.

In certain embodiments, the topical formulation may further include emulsifiers and dispersing agent(s)s which include, for example, anionic, cationic and nonionic surfactants. Nonionic surfactants are preferred because of their low levels of irritation to skin. Typical of nonionic surfactants are fatty acid monoglycerides such as glyceryl monostearate, etc.; sorbitan fatty acid esters such as sorbitan monolaurate, etc.; sucrose fatty acid esters; polyoxyethylene fatty acid esters such as polyoxyethylene stearate, etc.; and polyoxyethylene higher alcohol ethers such as polyoxyethylene cetyl ether, polyoxyethylene oleyl ether, etc.

In certain embodiments of the present invention, the topical formulation may include a gelling agent(s) such as methylcellulose, ethylcellulose, hydroxyethylcellulose, hydroxypropyl-cellulose, hydroxypropylmethylcellulose, carboxymethylcellulose, carbomer, and the like.

In certain embodiments of the present invention, the percentage of patients experiencing migraine or cluster headache pain relief may be significantly improved based on an aqueous based topical formulation. Some examples of patents disclosing pharmaceutical compositions which rely upon an aqueous gel composition as a excipient for the application of a drug are U.S. Pat. Nos. 4,883,660; 4,767,619; 4,511,563; 4,861,760; and 5,318,780, the disclosures of which are herein incorporated by reference.

The topical formulation may further include one or more preservatives, stabilizers, or anti-oxidants.

Examples of preservatives that may be used in a formulation according to the present invention include, but are not limited to, bateriostatic compounds and other preservatives suitable for topical administration including various alcohols, sorbic acid and salts and derivatives thereof, ethylenediamine, monothioglycerol, and thimerosal.

Examples of stabilizers that may be present in a formulation according to the present invention include pH buffers suitable for topical administration, complexing agent(s)s, chelating agent(s)s and the like.

Examples of anti-oxidants that may be used in a formulation according to the present invention include ascorbic acid and its derivatives, e.g., ascorbyl palmitate, as well as butylated hydroxyanisole, butylated hydroxytoluene, sodium bisulfite, sodium metabisulfite, and others.

Other excipients that may be included in the drug formulation include carriers, tackifiers, pigments, dyes, and other additives that do not adversely affect the mechanical or adhesive properties of the formulation.

"Excipients" as used herein refer to excipient materials suitable for transdermal drug administration, and include any such materials known in the art, e.g., any liquid, gel, emulsion, solvent, liquid diluent, solubilizer, or the like, which is nontoxic and which does not interact with other components of the composition in a deleterious manner. The term "excipient" as used herein may also refer to stabilizers, crystallization inhibitors, dispersing agent(s)s or other types of additives useful for facilitating transdermal drug delivery. It will be appreciated that compounds classified as "excipients" may sometimes act as permeation enhancers, and vice versa, and, accordingly, these two classes of chemical compounds or compositions may sometimes overlap.

Excipient materials suitable for use in the instant compositions include those well-known for use in the cosmetic and medical arts as bases for ointments, lotions, salves, aerosols, suppositories and the like. Suitable excipients include, for example, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable excipients herein include for example alcohols, including both monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

In certain embodiments, the present invention further provides for a method of manufacturing the formulations of the present invention comprising grinding the active agent(s) into fine particles; mixing the particles with a aqueous and/or organic solution to provide for a solution or dispersion of the active agent(s); filtering and rinsing the residue; preferably bringing the volume of the filtrate to that of the final product; preferably concentrating the filtrate (preferably using a low pressure vacuum) to 25% of the original volume; mixing the condensed filtrate with a requisite amount of a excipient (e.g., Lipoderm®); and preferably placing the final formulation in a metered dosing device (or alternatively, otherwise dividing the formulation into unit doses prior to use).

In certain embodiments, a topical gel formulation containing the active agent(s) described herein may be prepared by: i) mixing a requisite amount of active agent(s) with a requisite amount of Lecithin/Isopropyl Palmitate 50/50 gel; ii) thereafter adding a requisite amount of ethoxy diglycol liquid a requisite and a requisite amount of pluronic F127 20% to the mixture of step 1); and iii) placing the resultant formulation through an ointment mill to prepare unit doses of the ergot alkaloid gel formulation.

In certain other embodiments, a topical gel formulation containing the active agent(s) described herein may be prepared by: i) mixing a requisite amount of active agent(s) with a requisite amount of Lipoderm®; and ii) placing the resultant formulation through an ointment mill to prepare unit doses of the active agent(s) gel formulation.

In certain embodiments of the present invention, the formulations of the present invention may be formulated as a transdermal delivery system (also referred to herein as a transdermal therapeutic system) such as a transdermal patch, a transdermal plaster, a transdermal disc, iontophoretic transdermal device, or the like.

In certain embodiments, the active agent(s) containing transdermal delivery devices, as well as other transdermal delivery systems in accordance with the invention can be made in the form of an article such as a tape, a patch, a sheet, a dressing or any other form known to those skilled in the art. Generally the device will be in the form of a patch of a size suitable to deliver a unit dose of active agent(s) through the skin. The active agent(s) may be introduced into a transdermal therapeutic system in different forms (solid, in solution, in dispersion); it may also be microencapsulated. Generally, when the active agent(s) is present in a device of the invention, the active agent(s) is present in an amount by weight of about 1 to about 25 percent, preferably about 5 to 15 percent, by weight based on the total weight of the adhesive layer.

In certain embodiments the present invention provides a transdermal therapeutic system comprising an active agent(s) in an amount that would provide sub-therapeutic plasma levels if administered orally, but is therapeutically effective when administered via transdermal delivery at the affected region.

A transdermal delivery system for use in accordance with the present invention can also be constructed with an enhancer composition and other ingredients described hereinabove with respect to the topical formulation. Preferably the transdermal delivery system is formulated for the rapid delivery of an active agent(s) as would be beneficial to a person suffering from a migraine and/or cluster headache, muscle sprains, muscle spasms, spasticity, tension headache, tension-related migraines or other related conditions associated with muscle tension and pain. The targeted skin flux for delivery of a particular drug can be achieved by adjusting excipient composition and excipient loading, as well as by adjusting the surface area through which the compositions are administered to skin.

The transdermal delivery system used in the present invention may be prepared, for example, in accordance with U.S. Pat. Nos. 5,069,909; 4,806,341; 5,026,556; 4,588,580; 5,016,652; 3,598,122; 4,144,317; 4,201,211; 4,262,003; and 4,379,454; all of which are incorporated herein by reference.

In certain embodiments of the present invention, wherein the transdermal delivery system is a transdermal patch, the transdermal patch comprises a active agent(s) contained in a reservoir or a matrix, and an adhesive which allows the transdermal patch to adhere to the skin, allowing the passage of the active agent(s) from the transdermal patch through the skin of the patient. Once the active agent(s) has penetrated the skin layer, the active agent(s) is absorbed into the blood stream where it exerts the desired pharmaceutical effects.

In certain embodiments, the dosage form can be a transdermal patch comprising a laminated composite for administering the active agent(s) to an individual transdermally comprising: (a) a polymer backing layer that is substantially impermeable to the active agent(s); and (b) a reservoir layer comprising a water-base acrylate pressure-sensitive adhesive, 1 to 12% by weight active agent(s) and 2 to 25% by weight of a permeation enhancer comprising propylene glycol monolaurate in combination with capric acid or oleic acid, wherein the skin contact area of the composite is 10 to 100 cm$^2$.

The dosage form can be a transdermal patch comprising (a) a polar solvent material selected from the group consisting of $C_3$-$C_4$ diols, $C_3$-$C_6$ triols, and mixtures thereof; and (b) a polar lipid material selected from the group consisting of fatty alcohol esters, fatty acid esters, and mixtures thereof; wherein the polar solvent material and the polar lipid material are present in a weight ratio of solvent material:lipid material of from about 60:40 to about 99:1.

In certain embodiments, the dosage form also comprises a transdermal plaster comprising: a film layer which comprises a polyester film of 0.5 to 4.9:m thickness, 8 to 85 g/mm strength, respectively in the two directions intersecting substantially at right angles, 30 to 150% elongation, in the two directions intersecting substantially at right angles and an elongation ratio of A to B of 1.0 to 5.0, wherein A and B represent data in two directions intersecting at right angles, and A is greater than B, and wherein the polyester film comprises 0.01 to 1.0% by weight, based on the total weight of the polyester film, of solid fine particles in which (a) the average particle size is 0.001 to 3.0:m, and (b) the average particle size is substantially not more than 1.5 times the thickness of the polyester film; and an adhesive layer (a) which is composed of an adhesive containing the ergot alkaloid and further wherein the adhesive layer (a) is laminated on the film layer over the surface in a 2 to 60:m thickness.

In certain embodiments, the dosage form can be a transdermal disc comprising: (a) a backing layer which is substantially impervious to the active agent(s); and (b) a polymer matrix disc layer which is adhered to the backing layer and which has microdispersed therein the active agent(s), the polymer being bioacceptable and permitting the active agent(s) to be transmitted for transdermal absorption, the active agent(s) being stable in the polymer matrix.

In certain preferred embodiments, the treatment of the migraine and/or cluster headache, muscle sprains, muscle spasms, spasticity, tension headache, tension-related migraines or other related conditions associated with muscle tension and pain is by application of the transdermal therapeutic system (e.g., patch) comprising the active agent(s) to the affected region.

In certain embodiments, the present invention further provides for applying a topical formulation as described herein for the immediate release of the active agent(s) upon an acute attack, plus the application of a transdermal therapeutic system (e.g., a patch) for the prophylactic treatment of secondary attacks due to the delayed effect of the transdermal therapeutic system.

The present invention is contemplated to encompass all transdermal formulations, e.g., the technologies described above, with the inclusion of an active agent(s), such that the administration of the active agent(s) provides for the relief of pain or symptoms.

DETAILED DESCRIPTION OF THE PREFERRED EMBODIMENTS

The following examples illustrate various aspects of the present invention. They are not to be construed to limit the claims in any matter whatsoever.

EXAMPLE 1

Preparation of Tizanidine Transdermal Gel

Tizanidine transdermal gel was prepared by chemically extracting tizanidine from commercially available tablets and mixing the extracted tizanidine with a transdermal compounding medium, e.g., Lipoderm® to obtain a topical gel formulation containing 2 mg/ml of tizanidine. The tizanidine gel was placed into tuberculin syringes for administration.

Treatment Methods

Initial doses of 0.4 mg to 0.8 mg of tizanidine were administered with additional applications made after 15-30 minutes, up to a total of 4.0 mg tizanidine, as necessary in certain severe cases. The transdermal gel was applied by gentle rubbing of the gel into the effected muscle(s) using a gloved finger. In cases of spasticity, equal amounts of gel were applied to the extensor and flexor muscles involved.

Twenty-three (23) patients with a variety of clinically significant conditions of muscle spasms and spasticity were treated in an open-label study. The patients' specific complaints of muscle tightness and pain were confirmed by clinical exam in each situation. Fifteen patients had cervical and trapezius spasm, five had thoraco-lumbar spasm and one patient had both. Two patients had significant spasticity from prior stroke (See: Table 1 below):

TABLE 1

| Transdermal Tizanidine (Zanaflex ®): 0.4 mg-0.8 mg in Lipoderm | | | |
|---|---|---|---|
| Pt. # | Age | Diagnosis | minutes until relief |
| 1 | 76 | cervical muscle and trapezius muscle spasms | 3-5 min |
| 2 | 28 | cervical sprain and headaches | 2-5 min |
| 3 | 70 | lumbar radiculopathy, lumbar Para spinal spasm | 1 min |
| 4 | 28 | sore muscles of back and scapular muscle strain | 5-10 min |
| 5 | 59 | thoracic/lumbar pain; kyphoscoliosis | 30 min |

TABLE 1-continued

Transdermal Tizanidine (Zanaflex ®): 0.4 mg-0.8 mg in Lipoderm

| Pt. # | Age | Diagnosis | minutes until relief |
|---|---|---|---|
| 6 | 66 | cervical spondylosis | 10-15 min |
| 7 | 64 | cervical sprain, headaches-cervical muscles | 5-10 min |
| 8 | 59 | lumbar stenosis paraspinous spasticity | 4-5 min |
| 9 | 15 | cervical sprain, headaches, neck muscle spasms | 10-15 min |
| 10 | 77 | trapezius spasm, cervical spondylosis, Parkinson's | 3-5 min |
| 11 | 49 | cervical sprain, headaches | 3-5 min |
| 12 | 80 | cervical spondylosis, Parkinson's | 3-5 min |
| 13 | 43 | cervical spondylosis w/ bilateral trapezius spasm & HA's | 3-5 min |
| 14 | 56 | Lumbar radiculopathy & neuropathy | 15-20 min |
| 15 | 87 | cervical spondylosis | 3-4 min |
| 16 | 77 | cervical spondylosis w/ right cervical paraspinal trapezius spasm | 3-4 min |
| 17 | 24 | muscle contraction and migraine headaches-cervical | 5 min |
| 18 | 66 | Status post stroke w/ severe right upper extremity spasticity | 5-10 min |
| 19 | 42 | Cervical spondylosis with radiculopathy | 3-5 min |
| 20 | 37 | Cervical traction and cluster headaches | 5-6 min |
| 21 | 55 | Multiple sclerosis, lumbar & cervical muscle contraction & spondylosis | 10 min |
| 22 | 60 | cervical spondylosis | 5-10 min |
| 23 | 71 | Status post stroke w/ severe left upper extremity spasticity | 5-10 min |

The results of the clinical study of the twenty three patients showed that all patients treated with transdermal tizanidine experienced some relief of spasm and associated discomfort within 15 minutes of gel application. Some patients achieved near complete relief of symptoms by 60 minutes, which was corroborated by clinical exam. The more severe cases achieved partial, but clinically significant relief. Both stroke patients treated achieved some relief of spasticity. One patient, two months post stroke, achieved improvement to the extent he was able to straighten his affected arm and lift it above his head, something the patient had not been able to do before. The other stroke patient, 15 years post stroke suffering with severe symptoms, had slight, but definite improvement in movement at the elbow of her extremity. No local or systemic side effects were noted.

An additional 29 subjects have undergone the single-dose study since the original 23 patients were studied. These patients were treated in the clinic for a headache episode with transdermal tizanidine gel prepared according to example 1. Each patient received a single dose of tizanidine (either 0.5 mg or 1 mg) applied onto the posterior cervical muscles on the side of the headache. With bilateral headache, the dose was split between the two sides.

The patients were asked to characterize: a) headache type: i) migranous (throbbing head, pain, photophobia, sonophobia and nausea) or ii) muscle tension type involving the posterior cervical, occipital or temporal muscles; b) intensity of headache prior to treatment; iii) time to reduction of headache pain by at least 50%; and iv) side effects.

The additional results of the study indicated that both types of headache were relieved with topical tizanidine gel (Migraines 82%, muscle tension type 100%). Reduction in cervical muscle tension with improved range of motion was noted in all treated patients. Patients with migraine headache experienced reduction of light/sound sensitivity and nausea in addition to head pain relief.

Adverse events reported included transient warm feeling at the application site, slight lightheadedness and euphoria. There were no serious side effects and no significant lethargy, drowsiness or fatigue reported.

EXAMPLE 3

Ergot Alkaloid Transdermal Gel

Preparation of Methysergide Transdermal Gel

Methysergide transdermal gel is prepared by chemically extracting methysergide from commercially available tablets and mixing the extracted methysergide with a transdermal compounding medium, e.g., Lipoderm® to obtain a topical gel formulation containing methysergide 2 mg/ml. The methysergide gel is placed into tuberculin syringes for administration.

EXAMPLES 4-6

Sumatriptan/Additional Active Agent Transdermal Gel

A combination sumatriptan/additional active agent gel was produced with the formula set forth in Table 2 below:

TABLE 2

| Ingredient | Amt/unit (mg) |
|---|---|
| Imitrex ® (sumatriptan succinate) 100 mg tablet | 2200 mg (22 tablets) |
| Additional Active | * mg (** tablets) |
| Ethoxy Diglycol Liquid | 2.200 gm |
| Lecithin/Isopropyl Palmitate 50/50 gel | 4.400 gm |
| Pluronic F127 20% Liquid | 11.286 gm |

* See below for mg quantities of additional active agents
** See below for tablet amounts of additional active agents Dosage forms of the above formulation were prepared according to the following procedure:
1. 100 mg Imitrex® tablets (sumatriptan succinate) and the requisite amount of additional active agent tablets are crushed and mixed with Lecithin/Isopropyl Palmitate 50/50 gel.
2. Thereafter, the Ethoxy diglycol liquid is added and mixed together with 1.
3. The pluronic F127 20% is also added to the mixture.
4. The resultant formulation is put through an ointment mill and 1 ml unit doses are placed in 1 ml oral syringes. The syringes contain a gel having a sumatriptan concentration of 100 mg/ml and an active agent concentration of */ml.

I example 5, the additional active agent is methysergide 2 mg/ml (44 mg=22 tablets).

In example, the additional active agent is tizanidine 2 mg/ml (44 mg=11 tablets).

EXAMPLES 7-9

Transdermal Gel

An aqueous based sumatriptan/additional active agent gel was produced with the formula set forth in Table 3 below:

TABLE 3

| Ingredient | Amt/unit (mg) |
|---|---|
| Imitrex ® (sumatriptan succinate) 100 mg tablet | 2200 mg (22 tablets) |
| Additional Active Agent | * mg (** tablets) |
| Lipoderm ®/LIP*** | q.s. |

* See below for mg quantities of additional active agents
** See below for tablet amounts of additional active agents
***Lipoderm ®/LIP is a commercially marketed compounding agent(s) having the following ingredients: Ethoxydiglycol, Water (Aqua), Glycerin, C12-15 Alkyl Benzoate, Glyceryl Stearate, Dimethicone, Cetearyl Alcohol, Cetearyl Glucoside, Polyacrylamide, Cetyl Alcohol, Magnesium Aluminum Silicate, Xanthan Gum, Aloe Vera (Aloe Barbadensis), Tocopheryl Acetate (Vitamin E Acetate), Prunus Amygadalus Amara (Bitter Almond) Kernel Oil, Vitis Vinifera (Grape) Seed Extract, Triticum Vulgare (Wheat) Germ # Oil, Retinyl Palmitate (Vitamin A Palmitate), Ascorbyl Palmitate (Vitamin C Palmitate), Pro-Lipo Multi-emulsion Liposomic System, Tetrasodium EDTA, Phenoxyethanol, and Sodium Hydroxymethylglycinate.

Dosage forms of the above formulation in Table 2 were prepared according to the following procedure:
1. 100 mg Imitrex® tablets (sumatriptan succinate) are crushed and mixed with a sufficient amount of Lipoderm® to provide a sumatriptan concentration of 100 mg/ml.
2. The resultant formulation is put through an ointment mill and 1 ml unit doses are placed in 1 ml oral syringes. The syringes contain a gel having a sumatriptan concentration of 100 mg/ml.

In example 8, the additional active agent is methysergide 2 mg/ml (44 mg=22 tablets).

In example 9, the additional active agent is tizanidine 2 mg/ml (44 mg=11 tablets).

EXAMPLE 10

A sumatriptan/additional active agent (e.g., an ergot alkaloid, skeletal muscle relaxant) formulation having a final strength of 12.5/0.25 mg per 0.1 ml was prepared according to the following procedure:
1. Triturate the requisite amount of sumatriptan succinate and additional active agent tablets in a mortar and pestle to a small particle size.
2. Wet the powder with 95% ethyl alcohol and triturate. Add pure water and triturate again.
3. Filter and rinse the residue twice with enough water to bring the volume of the filtrate to that of the final product. For example, if preparing 100 ml of the transdermal migraine formulation, filter until the total volume of the filtrate reaches 100 ml.
4. Concentrate the filtrate using low pressure vacuum to 25% of the original volume (e.g., to 25 ml in the example).
5. Mix the condensed filtrate and Lipoderm® in mixing syringes to the desired volume (e.g., 100 ml in step 3).

The final strength is 12.5/0.25 mg of sumatriptan succinate/additional active per 0.1 ml.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification is accordingly to be regarded in an illustrative manner rather than a restrictive sense.

What is claimed is:

1. A method of treating migraines and cluster headaches with a topical formulation comprising applying a unit dose of a therapeutically effective amount of the active agent tizanidine or a pharmaceutically acceptable salt thereof incorporated into an immediate release pharmaceutically acceptable topical carrier onto the skin of a human patient experiencing an acute condition selected from the group consisting of migraine and cluster headache, at the posterior cervical area in close proximity to the brain stem, such that the unit dose provides a therapeutic effect within about 15 to about 30 minutes after topical administration to the human patient.

2. The method of claim 1, wherein the formulation further comprises a therapeutically effective amount of a serotonin agonist.

3. The method of claim 1, wherein the topical carrier is an aqueous based carrier.

4. The method of claim 1, wherein the topical formulation in a form selected from the group consisting of a liquid, a semisolid, a solid and mixtures thereof.

5. The method of claim 1, further comprising incorporating a therapeutic amount of the active agent into the unit dose such that the active agent would provide a subtherapeutic plasma level if orally administered, but is therapeutically effective when administered topically at the posterior cervical area.

6. The method of claim 1, wherein the unit dose further comprises a therapeutically effective amount of an ergot alkaloid selected from the group consisting of bromocriptine, ergocristine, ergocristinine, ergotamine, ergotaminine, ergocryptine, ergocryptinine, ergocornine, ergocorninine, ergosine, ergosinine, ergonovine, ergometrinine, dihydroergotamine, lisuride, d-lysergic acid, d-isolysergic acid, lysergol, lergotrile, metergoline, methysergide, methylergonovine, pharmaceutically acceptable salts thereof, and mixtures thereof.

7. The method of claim 6, wherein the ergot alkaloid is selected from the group consisting of dihydroergotamine base, dihydroergotamine mesylate, and mixtures thereof.

8. The method of claim 6, wherein the therapeutically effective amount of ergot alkaloid ranges from about 0.1 mg to about 10 mg, preferably from about 0.5 mg to about 6 mg.

9. The method of claim 1, wherein the unit dose comprises from about 0.2 mg to about 8 mg of tizanidine hydrochloride.

10. The method of claim 2, wherein the serotonin agonist is selected from the group consisting of sumatriptan, naratriptan, eletriptan, rizatriptan, zolmitriptan, almotriptan, frovatriptan, pharmaceutically acceptable salts thereof, and mixtures thereof.

11. The method of claim 10, wherein the serotonin agonist is sumatriptan.

12. The method of claim 11, wherein the unit dose comprises from about 0.5 mg to about 200 mg sumatriptan.

13. The method of claim 11, wherein the unit dose comprises from about 5 mg to about 50 mg sumatriptan.

14. The method of claim 1, further comprising incorporating one or more ingredients into the topical formulation selected from the group consisting of ethoxydiglycol, water, glycerine, C12-15alkyl benzoate, glyceryl stearate, dimethicone, cetearyl alcohol, cetearyl glucoside, polyacrylamide, cetyl alcohol, magnesium aluminum silicate, xanthan gum, aloe vera (aloe barbadensis), tocopheryl acetate (vitamin E acetate), prunus amygadalus amara (bitter almond) kernel oil, vitis vinifera (grape) seed extract, triticum vulgare (wheat) germ oil, retinyl palmitate (vitamin A palmitate), ascorbyl palmitate (vitamin C palmitate), pro-lipo multi-emulsion liposomic system, tetrasodium EDTA, phenoxyethanol, and sodium hydroxymethylglycinate.

15. The method of claim 1, wherein the unit dose comprises from about 0.2 mg to about 4 mg of tizanidine hydrochloride.

16. A method of treating migraines and cluster headaches with a topical formulation comprising applying a unit dose of from about 0.2 mg to about 8 mg of tizanidine hydrochloride and from about 0.5 mg to about 200 mg sumatriptan succinate, incorporated into a pharmaceutically acceptable carrier, onto the skin of a human patient experiencing an acute condition selected from the group consisting of migraine and cluster headache, at the posterior cervical area in close proximity to the brain stem of the human patient, such that the unit dose provides a therapeutic effect within about 15 to about 30 minutes after topical administration to the human patient.

17. The method of claim 16, wherein the unit dose comprises from about 0.4 mg to 4 mg of tizanidine hydrochloride and from about 5 mg to 50 mg sumatriptan succinate.

18. The method of claim 16, further comprising applying an additional unit dose onto the skin of the human patient at the posterior cervical area from about 15 minutes to about 3 hours after the first application of the unit dose.

19. The method of claim 16, wherein the topical formulation further comprises from about 0.1 mg to about 10 mg of an ergot alkaloid.

20. The method of claim 16, wherein the pharmaceutical acceptable carrier is aqueous-based.

* * * * *